United States Patent [19]

Holtkamp, Sr.

[11] Plant 4,578

[45] Jul. 22, 1980

[54] AFRICAN VIOLET PLANT

[76] Inventor: Hermann Holtkamp, Sr., Kueningsmuehle, 2 Dingden, 4236 Hamminkeln, Fed. Rep. of Germany

[21] Appl. No.: 23,474

[22] Filed: Mar. 23, 1979

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet having vigorous growth habit; strong and upright flower stems, each carrying 7–9 large single star-shaped purple-violet flowers; prominent bright yellow anther cells, and by its round to heart-shaped leaves carried on strong petioles.

1 Drawing Figure

The present invention comprises a new and distinct cultivar of African violet plant, botanically known as *Saintpaulia ionantha,* and hereinafter referred to by the cultivar name Pamela.

The new cultivar was referred to during the breeding and selection process by the designation XXI/3 - 94/79, and is a product of a planned breeding program. The new cultivar is principally characterized by its large, star-shaped purple-violet flowers carried on strong upright stems. The large flowers, 7–9 of which are carried on each stem, together with bright yellow anther cells, provide a highly attractive, dense bouquet.

The new cultivar was originated from a cross made in a controlled breeding program in Isselburg, Rhineland, Germany. The female, or seed parent was a cultivar designated XIX 4020 blue-violet, unpatented.

The new cultivar was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of the new cultivar, Pamela, which in combination distinguish this African violet as a new and distinct cultivar:

(1) Vigorous growth habit.

(2) Strong and upright flower stems, with 7–9 large single star-shaped flowers carried on each stem, producing a full flower bouquet.

(3) Flowers are very long lasting and don't drop.

(4) Purple-violet flower color.

(5) Leaves are round to heart-shaped, slightly hairy, and carried on strong petioles which are very hairy.

(6) Prominent bright yellow anther cells, which provide a pleasant contrast with the large purple-violet flowers.

The accompanying photographic drawing shows a typical specimen plant of the new cultivar. The colors appearing in the photograph are as true as possible with color illustrations of this type.

In the following description, color references are made both to the Royal Horticultural Society color chart (RHS) and the Horticultural Colour Chart (HCC) issued by Wilson Colour Ltd., except where general color terms of ordinary significance are obvious.

Botanical classification: *Saintpaulia ionantha,* Ramat. cv Pamela.

Parentage:

*Male parent.*—XX 94 lilac star-shaped.

*Female parent.*—XIX 4020 blue-violet.

Propagation: The new cultivar holds its distinguishing characteristics through successive propagations by leaf cuttings and by division of shoots.

Plant: From 10 cm. to 12 cm. tall when grown in pots, and approximately 25–30 cm. in diameter when fully grown.

*Leaves.*

*General form.*—Round to heart-shaped.

*Diameter.*—65–70 mm.

*Texture.*—Soft.

*Aspect.*—Velvety, shiny smooth border, hairy.

*Veins.*—Well pronounced, hairy, green-reddish, on younger leaves areas between main veins are small thin branches violet in color which are not visible on mature leaves.

*Color (upperside).*—RHS yellow-green 147 A.

*Color (underside).*—HCC leek green 000858.

*Petiole.*—Strong, round, very hairy; color on older leaves medium green-reddish, young leaves brown-red.

Flowers:

*Buds.*—Bell-shaped, 7–9 mm. before opening, HCC bishops violet 34, turning rapidly after opening to light purple.

*Sepals.*—5 in number. Color: RHS grey brown 199 A. Calyx: funnel shaped. Aspect: spear-shaped hairy. Peduncle: erect, wirelike brownish-green.

Individual flowers:

*Size.*—45–50 mm.

*Color.*—Upperside: RHS purple-violet 82 C. Underside: RHS purple-violet 82 D.

*Borne.*—Five (5) equal size petals, slightly wavy edges, a few flowers have additional petals.

*Shape.*—Star-shaped.

*Arrangement.*—7–9 single flowers per flower stem, with the stems being carried on strong and wire-like peduncles.

*Flowering time.*—Uniform 7–8 weeks to first blooming after potting a well established starter into 3 or 4 inches pot; plant shows the full flowerhead in 8–10 weeks.

Reproductive organs:

*Stamens.*—4–5 in number.

*Anthers.*—8–10 anther cells carried on short, flat stems; yellow-green in color RHS yellow-orange 15 B.

*Arrangement.*—4–5 filament are around the seed-buds connected with receptacle.

*Filaments.*—4–5 short, flat, 3–4 mm. in length.

*Pollen color.*—RHS yellow-orange 15 D.

Roots: Well developed fine roots, hairy; well branched, color white brownish, lips white.

Disease resistance: No disease noticed to date.

General observations: This new cultivar with its large purple-violet flower, prominent anther cells, and full bouquet is highly attractive. It is a vigorous grower and no problems have been experienced to date with cultivation of the variety.

I claim:

1. A new and distinct cultivar of African violet as shown and described, characterized by the combined features of vigorous growth habit; strong and upright flower stems, each carrying 7–9 large single star-shaped purple-violet flowers; prominent bright yellow anther cells, and by its round to heart-shaped leaves carried on strong petioles.

* * * * *

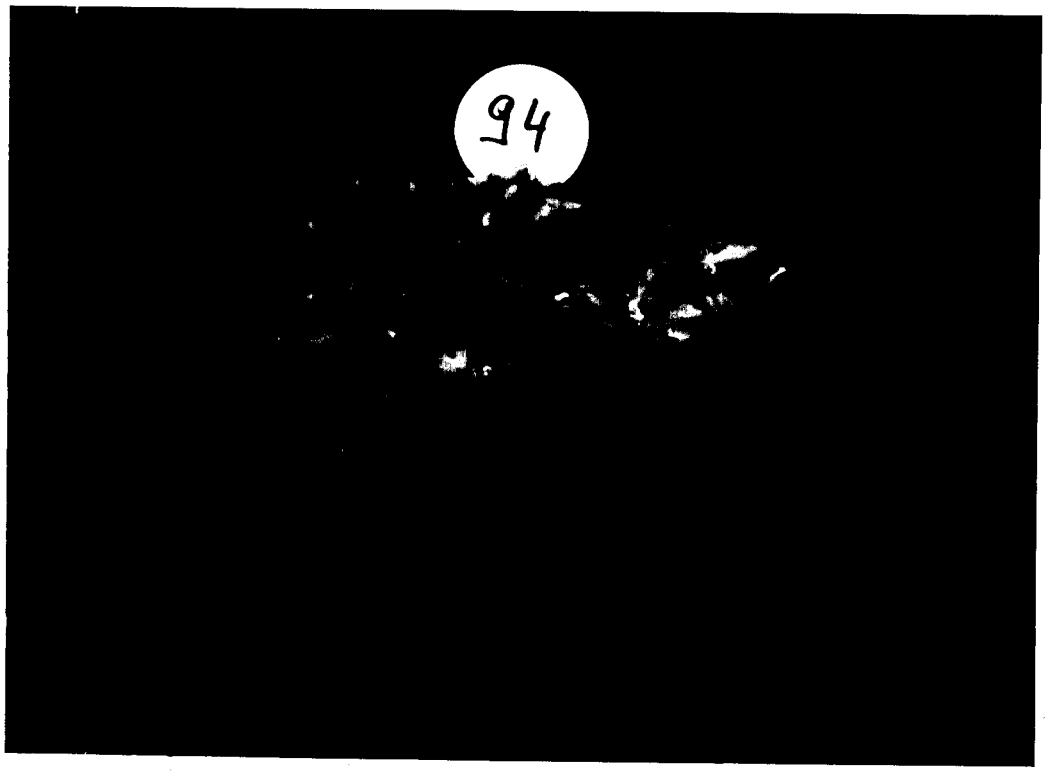
94